United States Patent
Sakaue et al.

(10) Patent No.: US 11,471,064 B2
(45) Date of Patent: Oct. 18, 2022

(54) IN VIVO POTENTIAL MEASUREMENT DEVICE

(71) Applicant: Toray Industries, Inc., Tokyo (JP)

(72) Inventors: Yusuke Sakaue, Otsu (JP); Chisa Inaka, Otsu (JP); Tatsuya Okada, Otsu (JP)

(73) Assignee: TORAY INDUSTRIES, INC., Tokyo (JP)

( * ) Notice: Subject to any disclaimer, the term of this patent is extended or adjusted under 35 U.S.C. 154(b) by 876 days.

(21) Appl. No.: 16/364,659

(22) Filed: Mar. 26, 2019

(65) Prior Publication Data

US 2019/0298220 A1   Oct. 3, 2019

(30) Foreign Application Priority Data

Mar. 27, 2018   (JP) .............................. JP2018-060487

(51) Int. Cl.
*A61B 5/0538*   (2021.01)
*A61B 5/00*   (2006.01)
(Continued)

(52) U.S. Cl.
CPC .......... *A61B 5/0538* (2013.01); *A61B 5/6853* (2013.01); *A61B 5/6885* (2013.01); *A61B 18/1492* (2013.01); *A61B 2018/0022* (2013.01); *A61B 2018/00285* (2013.01); *A61B 2018/00577* (2013.01); *A61B 2018/00595* (2013.01);
(Continued)

(58) Field of Classification Search
CPC ... A61B 5/0538; A61B 5/6853; A61B 5/6885; A61B 18/1492; A61B 2018/0022; A61B 2018/00285; A61B 2018/00577; A61B 2018/00595; A61B 2018/00875; A61B 2018/0212; A61B 2018/046; A61B 2018/147; A61B 2562/0214; A61B 2018/00351; A61B 2018/00702; A61B 2018/00892; A61B 2018/1472; A61B 5/282; A61B 5/283; A61B 5/6852;
(Continued)

(56) References Cited

U.S. PATENT DOCUMENTS

2002/0068931 A1* 6/2002 Wong ................. A61B 18/1206
606/41
2016/0199126 A1* 7/2016 Satake ............... A61B 18/1492
606/34

FOREIGN PATENT DOCUMENTS

JP   5870694 B2   3/2016

\* cited by examiner

*Primary Examiner* — Eun Hwa Kim
*Assistant Examiner* — Mystee Nguyen Delgado
(74) *Attorney, Agent, or Firm* — Global IP Counselors, LLP (57) ABSTRACT

An in vivo potential measurement device includes an insulating member and an amplifier. The insulating member has an electrode. The insulating member is inserted into an organ of a living body such that an outer peripheral face of the insulating member contacts with an inner wall face of the organ at a contact site. The electrode senses electric potential at the contact site. The amplifier amplifies the electric potential to obtain output voltage. The amplifier has input capacitance Cin and input resistance Rin that satisfy Cin/Ce>0.1 and $1/(2\pi f C_e R_{in})>0.1$, where Ce represents capacitance of the insulating member at the contact site, and f represents frequency of the electric potential at the contact site on the inner wall face. A contact state between the outer peripheral face and the inner wall face is evaluated using the output voltage.

20 Claims, 4 Drawing Sheets

(51) Int. Cl.
*A61B 18/14* (2006.01)
*A61B 18/00* (2006.01)
*A61B 18/02* (2006.01)
*A61B 18/04* (2006.01)

(52) U.S. Cl.
CPC .............. *A61B 2018/00875* (2013.01); *A61B 2018/0212* (2013.01); *A61B 2018/046* (2013.01); *A61B 2018/147* (2013.01); *A61B 2562/0214* (2013.01)

(58) Field of Classification Search
CPC ......... A61B 5/277; A61B 5/6886; A61B 5/72; A61B 5/722
USPC ....... 600/547, 301, 372, 373, 505, 549, 442, 600/506
See application file for complete search history.

IN VIVO POTENTIAL MEASUREMENT DEVICE

CROSS-REFERENCE TO RELATED APPLICATIONS

This application claims priority to Japanese Patent Application No. 2018-060487 filed on Mar. 27, 2018. The entire disclosure of Japanese Patent Application No. 2018-060487 is hereby incorporated herein by reference.

BACKGROUND

Field of the Invention

The present invention relates to an in vivo potential measurement device that is inserted into an organ of a living body and measures the electric potential at a specific site on an inner wall face of the organ.

Background Information

A catheter is inserted into a blood vessel or other such organ to examine or treat a lesion site.

One type of treatment using a catheter is ablation with a catheter equipped with a balloon. This treatment is performed by attaching a balloon to the tip of the catheter, inflating the balloon by injecting a liquid into it, and then warming the liquid in the balloon with a high-frequency current, thereby cauterizing the organ in contact with the surface of the balloon. This is used in the treatment of atrial fibrillation and the like, for example.

With this treatment, since the balloon has a flexible bulbous shape, the outer peripheral face of the inflated balloon can be brought into ring-shaped contact with the inner wall face near the junction between the pulmonary vein and the left atrium, which is the site where the atrial fibrillation is to be treated, so the area around the pulmonary vein can be cauterize all at once.

After an organ has been cauterized by ablation, the electric potential at the organ near the cauterization is measured in order to confirm the cauterizing effect. For example, Japanese Patent No. 5,870,694 (Patent Literature 1) discloses a method in which a catheter equipped with a plurality of electrodes for potential measurement at its tip is inserted into an organ, the electrodes are brought into contact with the organ near the cauterization, and the electric potential is measured at the sites where the electrodes are in contact.

SUMMARY

In ablation with a catheter equipped with a balloon, if there is a poor state of contact between the outer peripheral face of the inflated balloon and the inner wall face of the organ, the heat of the balloon will not be sufficiently transferred to the organ, so the desired cauterizing effect cannot be obtained.

The shape of the balloon can be ascertained by injecting a diluted contrast agent into the balloon and imaging with an X-ray CT (computed tomography) device, but organs such as cardiac tissue cannot be imaged with an X-ray CT apparatus, which means that the contact state between the balloon and the organ cannot be confirmed.

The current method use to confirm the state of contact between the balloon and the organ is to discharge the contrast medium from the tip of the balloon into the organ in a state in which the outer peripheral face of the balloon is pressed snugly against the inner wall face of the organ (an occluded state), and then check the state of contact by using an X-ray CT apparatus to see if the discharged contrast agent is not flowing out from the contacted organ (occlusion contrast enhancement).

However, it is difficult to perform the above-mentioned occlusion contrast enhancement during ablation treatment, for example, so the contact state cannot be checked in real time. Also, checking the contact state by occlusion contrast enhancement requires three-dimensional imaging, so the X-ray CT apparatus ends up being quite large.

The present invention was conceived in light of the above problems, and its main object is to provide an in vivo potential measurement device with which an insulating member having an electrode disposed inside is inserted into an organ of a living body, and the electric potential at a specific site on the inner wall face of the organ is measured, wherein a contact state in which the outer peripheral face of the insulating member is in contact with the inner wall face of the organ can be evaluated in real time.

The in vivo potential measurement device pertaining to the present invention is an in vivo potential measurement device that comprises an insulating member and an amplifier. The insulating member has an electrode that is disposed inside thereof. The insulating member is configured to be inserted into an organ of a living body such that an outer peripheral face of the insulating member contacts with an inner wall face of the organ at a contact site. The electrode is configured to sense electric potential at the contact site. The amplifier is configured to amplify the electric potential sensed by the electrode to obtain output voltage, the amplifier being configured to be disposed outside the living body. The amplifier has input capacitance Cin and input resistance Rin that satisfy $Cin/Ce > 0.1$ and $1/(2\pi f CeRin) > 0.1$, where Ce represents capacitance of the insulating member at the contact site, f represents frequency of the electric potential at the contact site on the inner wall face of the organ. A contact state between the outer peripheral face of the insulating member and the inner wall face of the organ is evaluated using the output voltage obtained by amplifying the electric potential sensed by the electrode with the amplifier.

In a preferred embodiment of the present invention, the amplifier includes a first amplifier having input capacitance Cin and input resistance Rin that satisfy $Cin/Ce > 0.1$ and $1/(2\pi f CeRin) > 0.1$, and a second amplifier having input capacitance Cin and input resistance Rin that satisfy $Cin/Ce < 0.01$ and $1/(2\pi f CeRin) < 0.01$. The contact state between the outer peripheral face of the insulating member and the inner wall face of the organ is evaluated using a voltage ratio $V_1/V_2$ of a first voltage $V_1$ obtained by amplifying the electric potential with the first amplifier and a second voltage $V_2$ obtained by amplifying the electric potential with the second amplifier.

The present invention provides an in vivo potential measurement device for measuring the electric potential at a specific site (e.g., contact site) on the inner wall face of an organ by inserting an insulating member having an electrode disposed inside into an organ of a living body, wherein a contact state in which the outer peripheral face of the insulating member is in contact with the inner wall face of the organ can be evaluated in real time.

DETAILED DESCRIPTION OF EMBODIMENTS

Selected embodiments of the present invention will now be described in detail with reference to the drawings. The present invention is not limited to or by the following embodiment. Also, appropriate modifications are possible within a range not deviating from the range that produces the effect of the present invention.

Figure 1:
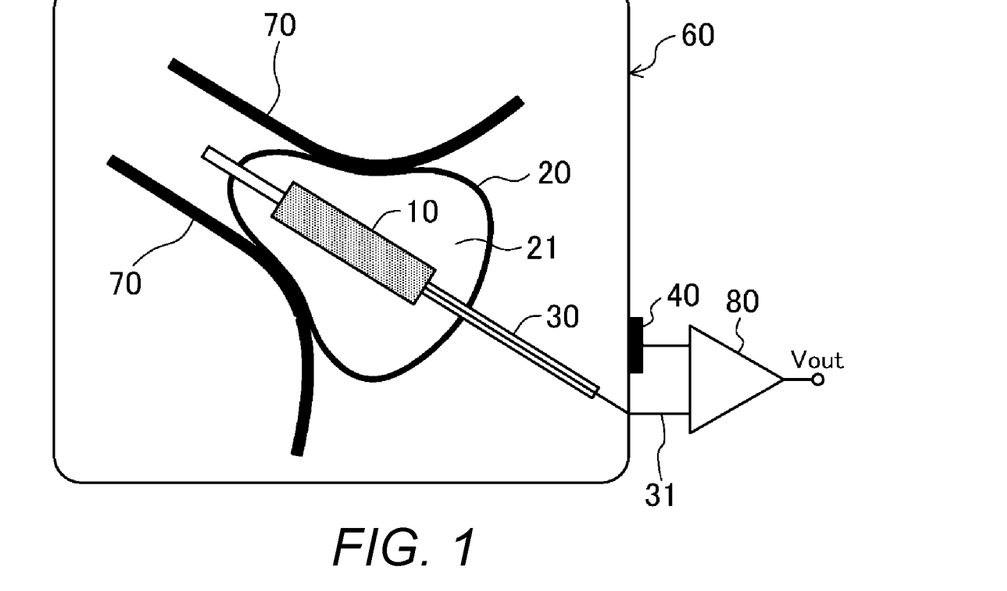
FIG. 1 is a simplified diagram of the basic configuration of an in vivo potential measurement device in an embodiment of the present invention.

FIG. 1 is a simplified diagram of the basic configuration of the in vivo potential measurement device in an embodiment of the present invention. The in vivo potential measurement device of the present invention is inserted into an organ of a living body and measures the electric potential at a specific site (e.g., a contact site) on the inner wall face of the organ. For example, it is used in the catheter ablation of atrial fibrillation to measure the electric potential at the cauterized site after cauterization.

As shown in FIG. 1, the in vivo potential measurement device in this embodiment comprises an insulating member 20 whose outer peripheral face can be deformed or expanded, and an electrode 10 disposed in the insulating member 20. A balloon in the form of a hollow pouch can be used as the insulating member 20, for example. Also, a balloon-equipped catheter in which a hollow, tubular, flexible member (catheter) 30 is coupled to the insulating member 20 may be used.

FIG. 1 shows a state in which the outer peripheral face of the insulating member 20 has been brought into contact with the inner wall face of a living organ 70 in a ring shape by injecting a conductive fluid 21 into the insulating member 20. For instance, in the case of catheter ablation treatment, the outer peripheral face of the insulating member 20 is brought into contact in a ring shape with the inner wall face of the organ near the junction between the pulmonary vein and the left atrium, which is the portion to be treated for atrial fibrillation. Here, the conductive fluid 21 can be injected from the outside via a hollow, tubular, flexible member (catheter) 30, for example. Physiological saline or the like can be used as the conductive fluid 21, for example.

As shown in FIG. 1, with the in vivo potential measurement device in this embodiment, in a state in which the outer peripheral face of the insulating member 20 is in contact in a ring shape with the inner wall face of the organ 70, the electric potential at the contact site is measured by the electrode 10 disposed in the insulating member 20.

As shown in FIG. 1, the electric potential at the site where the insulating member 20 is in contact can be measured by affixing a reference ground electrode 40 to the surface 60 of a living body, and using an amplifier 80 disposed outside the living body to amplify the voltage between the ground electrode 40 and the electrode 10 disposed in the insulating member 20. The electric potential at the electrode 10 is inputted to the amplifier 80 via a lead wire 31.

The insulating member 20 in this embodiment may also have the function (ablation function) of cauterizing the site where the insulating member 20 is in contact by passing a high-frequency current through the electrode 10 disposed in the insulating member 20 to heat the fluid 21 in a state in which the outer peripheral face of the insulating member 20 is in contact with the inner wall face of the organ.

Figure 2:
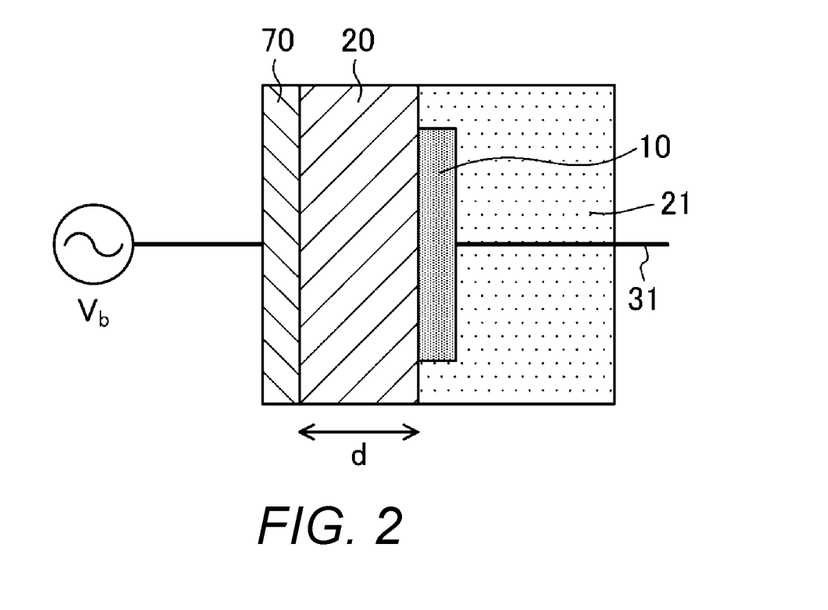
FIG. 2 is a simplified diagram a state in which the outer peripheral face of an insulating member is in contact with the inner wall face of an organ.

FIG. 2 is a simplified diagram of a state in which the outer peripheral face of the insulating member 20 is in contact with the inner wall face of the organ 70. Here, since the fluid 21 injected into the insulating member 20 is electrically conductive, the electric potential at the inner wall face of the insulating member 20 in contact with the fluid 21 is believed to be substantially the same as the electric potential at the electrode 10 disposed in the insulating member 20. Therefore, as shown in FIG. 2, the electrode 10 and the inner wall face of the organ 70 constitute a capacitance coupled electrode, with the insulating member 20 interposed in between.

Figure 3:
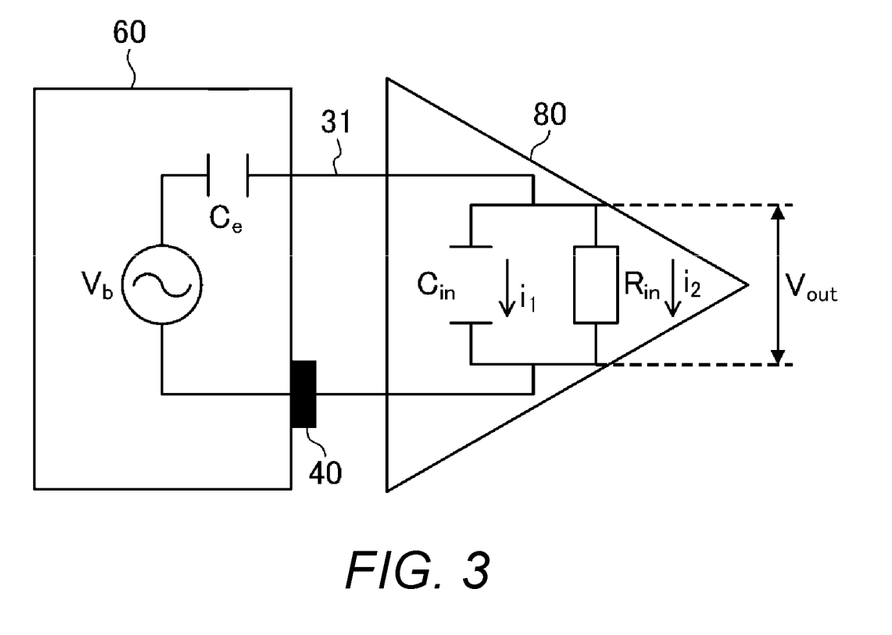
FIG. 3 is an equivalent circuit diagram showing a method in which the electric potential at a site where the outer peripheral face of the insulating member is in contact with the inner wall face of the organ is measured with an electrode disposed in the insulating member.

FIG. 3 is an equivalent circuit diagram showing the method by which the electric potential at the site where the outer peripheral face of the insulating member 20 is in contact with the inner wall face of the organ 70 is measured with the electrode 10 disposed in the insulating member 20. Here, Vb is the electric potential measured at the site where the outer peripheral face of the insulating member 20 is in contact with the inner wall face of the organ 70, and Ce is the capacitance between the electrode 10 and the organ 70. Vb is measured at the contact site as the one originated from the barycentric potential of a plurality of potentials around the organ 70. Also, the reference ground electrode 40 is affixed to the surface 60 of the living body, and the voltage between the electrode 10 and the ground electrode 40 is amplified by the amplifier 80 and measured or obtained as the output voltage Vout. Cin is the input capacitance of the amplifier 80, and Rin is the input resistance of the amplifier 80.

According to Kirchhoff's second law, we obtain the following Formula (1) in the equivalent circuit shown in FIG. 3.

$$V_b - Z_{Ce}(i_1 + i_2) - Z_{Cin} i_1 = 0 \tag{1}$$

Zce here is the impedance of the capacitance Ce between the electrode 10 and the organ 70, and Zcin is the impedance of the input capacitance Cin of the amplifier 80.

Also, in the closed-loop circuit of the amplifier 80, we obtain the following Formula (2) according to Kirchhoff's first law.

$$Z_{Cin} i_1 = R_{in} i_2 \tag{2}$$

Solving for $i_2$ using Formulas (1) and (2) yields the following Formula (3).

$$i_2 = \frac{V_b}{\frac{Z_{Ce} R_{in}}{Z_{Cin}} + Z_{Ce} + R_{in}} \tag{3}$$

Also, from Ohm's law, we obtain the following Formula (4).

$$V_{out} = R_{in} i_2 \tag{4}$$

Plugging Formula (3) into Formula (4) we obtain the following Formula (5).

$$\frac{V_{out}}{V_b} = \frac{1}{\frac{Z_{Ce}}{Z_{Cin}} + \frac{Z_{Ce}}{R_{in}} + 1} \quad (5)$$

The first and second terms of the denominator in Formula (5) are expressed by Formulas (6) and (7), respectively.

$$\frac{Z_{Ce}}{Z_{Cin}} = \frac{1}{j\omega C_e} \times jwC_{in} = \frac{C_{in}}{C_e} \quad (6)$$

$$\frac{Z_{Ce}}{R_{in}} = \frac{1}{j\omega C_e R_{in}} \quad (7)$$

Plugging Formulas (6) and (7) into Formula (5) we obtain the following Formula (8).

$$\frac{V_{out}}{V_b} = \frac{1}{\frac{C_{in}}{C_e} + \frac{1}{j\omega C_e R_{in}} + 1} \quad (8)$$

Here, if the right side of Formula (8) is expressed as K(Ce) (where K is a function of Ce), Formula (8) is expressed by the following Formula (9).

$$V_{out} = K(Ce)Vb \quad (9)$$

In Formula (9), the electric potential V b at the site where the insulating member 20 is in contact is changed by cauterization in the ablation treatment.

Meanwhile, if we let S be the contact surface area between the insulating member 20 and the organ 70, and let d be the thickness of the insulating member 20 (see FIG. 2), the capacitance Ce between the electrode 10 and the organ 70 is expressed by the following Formula (10).

$$C_e = \varepsilon_0 \varepsilon_r S/d \quad (10)$$

Here, $\varepsilon_0$ is the dielectric constant in a vacuum (8.855× $10^{-12}$ [F/m]), and $\varepsilon_r$ is the relative permittivity of the insulating member 20.

Therefore, in Formula (9), K(Ce) is a function of the contact surface area S between the insulating member 20 and the organ 70, and varies with the contact state.

That is, the output voltage Vout between the electrode 10 and the ground electrode 40 varies depending on the cauterization produced by ablation treatment and on the contact state between the insulating member 20 and the organ 70. Accordingly, the contact state between the insulating member 20 and the organ 70 cannot be confirmed merely by measuring the output voltage Vout between the electrode 10 and the ground electrode 40.

In view of this, the inventors turned their attention to the face that if the input capacitance Cin of the amplifier 80 is set sufficiently low and the input resistance Rin is set sufficiently high so as to satisfy Cin/Ce<0.01 and 1/(ωCeRin)<0.01 in the above Formula (8), then Formula (8) is expressed by the following Formula (11).

$$V_{out} = V_b \quad (11)$$

That is, the voltage between the electrode 10 and the ground electrode 40 is measured after being amplified by the amplifier 80 whose input capacitance Cin and input resistance Rin have been set so as to satisfy the above-mentioned conditions, which allows the electric potential Vb at the site of the organ 70 to be measured without being affected by the contact state between the insulating member 20 and the organ 70.

In view of this, the inventors arrived at the present invention upon realizing that a change in K(Ce), that is, a change in the contact state between the insulating member 20 and the organ 70, can be evaluated by measuring the voltage Vout with the amplifier 80 under the condition of not satisfying Formula (11), based on Formula (9), where the voltage Vout measured by the amplifier 80 under the condition of satisfying Formula (11) is a constant Vb.

Figure 4:
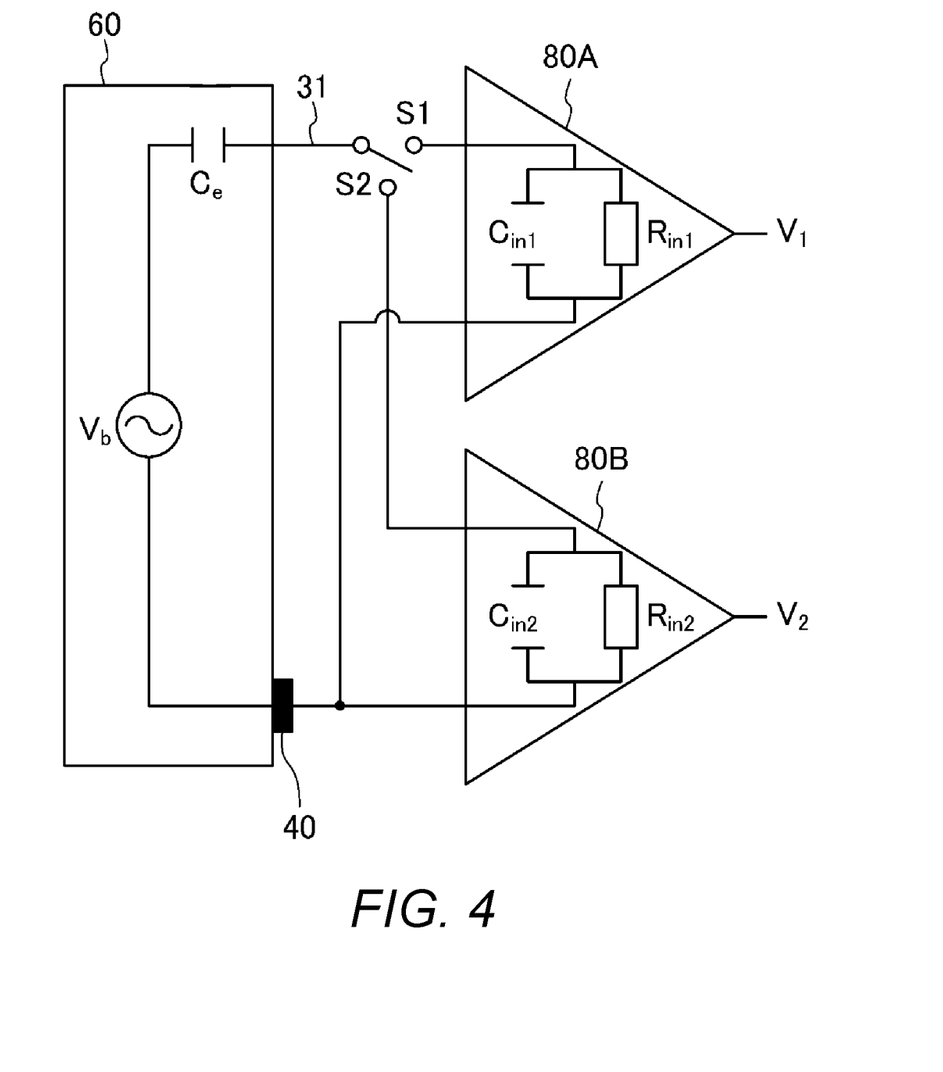
FIG. 4 is an equivalent circuit diagram showing the simplified configuration of the in vivo potential measurement device in another embodiment of the present invention.

FIG. 4 is a simplified equivalent circuit diagram of the configuration of the in vivo potential measurement device in an embodiment of the present invention.

The basic configuration of the in vivo potential measurement device in this embodiment is as shown in FIG. 1. That is, the insulating member 20 having the electrode 10 disposed inside is inserted into the organ 70 of a living body, and in a state in which the outer peripheral face of the insulating member 20 is in contact with the inner wall face of the organ 70, the electric potential at the contact site is measured with the electrode 10 disposed inside the insulating member 20.

As shown in FIG. 1, the electric potential at the site where the insulating member 20 is in contact can be measured by affixing the ground electrode 40 serving as a reference to the surface 60 of the living body, and using the amplifier 80 disposed outside the living body to amplify the voltage between the ground electrode 40 and the electrode 10 disposed in the insulating member 20. The electric potential at the electrode 10 is inputted to the amplifier 80 via the lead wire 31.

As shown in FIG. 4, the in vivo potential measurement device in this embodiment comprises a first amplifier 80A and a second amplifier 80B as the amplifiers that amplify the voltage between the ground electrode 40 and the electrode 10 disposed in the insulating member 20.

The first amplifier 80A is set to satisfy Cin1/Ce>0.1 and 1/(2πfCeRin1)>0.1, where Cin1 is the input capacitance and Rin1 is the input resistance. Also, the second amplifier 80B is set to satisfy Cin2/Ce<0.01 and 1/(2πfCeRin2)<0.01, where Cin2 is the input capacitance and Rin2 is the input resistance. Ce here is the capacitance at the site where the outer peripheral face of the insulating member 20 is in contact with the inner wall face of the organ 70, and f (=ω/2π) is the frequency band (e.g., frequency) at the contact site.

As shown in FIG. 4, the voltage between the ground electrode 40 and the electrode 10 disposed in the insulating member 20 is measured after being amplified by the first amplifier 80A or the second amplifier 80B, switching from one to the other with switching means (switches S1 and S2).

The voltage (first voltage) $V_1$ measured by amplifying the voltage between the ground electrode 40 and the electrode 10 disposed in the insulating member 20 with the first amplifier 80A is given by the following Formula (12) from the above-mentioned Formula (9).

$$V_1 = K(Ce)Vb \quad (12)$$

K(Ce) here is represented by the right side of the above-mentioned Formula (8).

Meanwhile, the voltage (second voltage) $V_2$ measured by amplifying the voltage between the ground electrode 40 and the electrode 10 disposed in the insulating member 20 with the second amplifier 80B is given by the following Formula (13) from the above-mentioned Formula (11).

$$V_2 = V_b \quad (13)$$

Here, when the switches S1 and S2 are switched at high speed, the electric potential Vb at the site where the insulating member 20 is in contact is considered to be substantially constant. Therefore, the above Formulas (12) and (13) give K(Ce) in the following Formula (14).

$$K(Ce)=V_1/V_2 \quad (14)$$

As described above, K(Ce) is a function of the contact surface area S between the insulating member 20 and the organ 70. Accordingly, when the value of $V_1/V_2$ changes from the above Formula (14), the contact surface area S between the insulating member 20 and the organ 70 changes.

Figure 5:
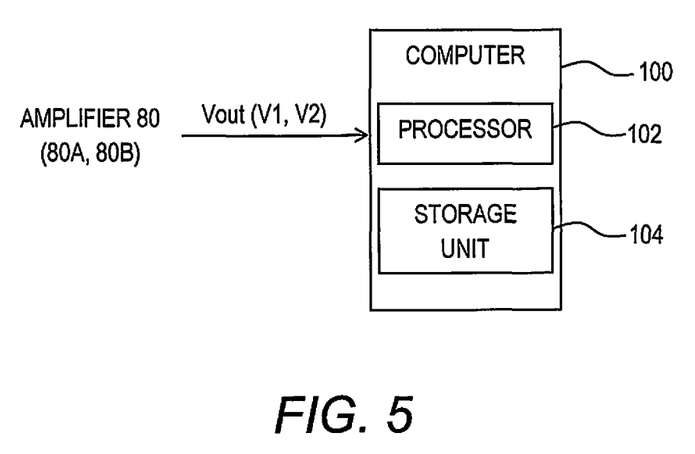
FIG. 5 is a block diagram of a computer of the in vivo potential measurement device.

That is, with the in vivo potential measurement device in this embodiment, the voltage ratio $V_1/V_2$ of the first voltage $V_1$ measured by amplifying with the first amplifier 80A and the second voltage $V_2$ measured by amplifying with the second amplifier 80B can be used to evaluate the contact state in which the outer peripheral face of the insulating member 20 is in contact with the inner peripheral face (inner wall face) of the organ 70. Consequently, the contact state between the insulating member 20 and the organ 70 can be checked in real time. Specifically, in the illustrated embodiment, the in vivo potential measurement device can further include a computer 100 that is configured to evaluate the contact state, as shown in FIG. 5. The computer 100 is electrically connected to the amplifier 80 (the first and second amplifier 80A and 80B) to measure the voltage Vout (the first and second voltages $V_1$ and $V_2$). The computer 100 calculates K(Ce) based on the voltage Vout (the first and second voltages $V_1$ and $V_2$) in a manner described in the present disclosure to evaluate the contact state. For example, the computer 100 can determine a change in the calculated value of K(Ce) to determine a change in the contact surface area S (i.e., a change of the contact state). In the illustrated embodiment, as illustrated in FIG. 5, the computer 100 includes at least one processor 102 having a CPU (Central Processing Unit) and the like, a storage unit 104 (computer memory) having a ROM (Read Only Memory), a RAM (Random Access Memory), a storage device, an input interface and the like. The storage device is, for example, a hard disk drive, a semiconductor storage device and the like. The computer 100 can evaluate the contact state by causing the processor 102 to execute a program that is stored in the storage unit 104. The input interface is electrically connected to the amplifier 80 (the first and second amplifier 80A and 80B) to obtain the voltage Vout (the first and second voltages $V_1$ and $V_2$) from the amplifier 80 (the first and second amplifier 80A and 80B) and measure the voltage Vout (the first and second voltages $V_1$ and $V_2$).

For example, during ablation treatment, in a state in which the outer peripheral face of the insulating member 20 is in contact with the inner wall face of the organ 70, a high-frequency current is passed through the electrode 10 to cauterize the contact site, and then the first voltage $V_1$ and the second voltage $V_2$ are measured, which allows the contact state between the insulating member 20 and the organ 70 immediately after cauterization to be evaluated. Consequently, ablation treatment can be performed while constantly monitoring the contact state between the insulating member 20 and the organ 70, so cauterization of the treatment site can be reliably carried out.

Also, with conventional occlusion contrast enhancement, a large-scale X-ray CT apparatus is required to check the contact state in three dimensions, but with this embodiment, all that is necessary is to insert the insulating member 20 inside of which the electrode 10 is disposed into the organ 70 of the living body and measure the electric potential at the site in contact with the insulating member 20, so the contact state between the insulating member 20 and the organ 70 can be checked with a simple device.

In the above embodiment, a situation was described in which the switching between the first amplifier 80A and the second amplifier 80B was performed at high speed, but there are no particular restrictions on the timing as long as it allows the electric potential Vb at the site where the insulating member 20 is in contact is to be substantially constant. For example, if the electric potential Vb in the organ 70 with which the insulating member 20 is in contact fluctuates at a constant cycle, switching may be performed at this same cycle. In this case, after the first voltage $V_1$ is measured with the first amplifier 80A at a certain timing, the second voltage $V_2$ may be measured with the second amplifier 80B at a point several cycles later.

The above embodiment was premised on the fact that the electric potential Vb at the site where the outer peripheral face of the insulating member 20 is in contact with the inner wall face of the organ 70 changes due to cauterization by ablation treatment or the like, but the contact state between the insulating member 20 and the organ 70 can also be evaluated by using the in vivo potential measurement device of this embodiment when Vb is constant or changes periodically. An example of when the electric potential Vb is constant is the myoelectric potential. An example of when the electric potential Vb changes periodically is the cardiac potential.

In this case, the electric potential Vb at the site where the insulating member 20 is in contact is measured by using the first amplifier 80A to amplify the electric potential sensed by the electrode 10 disposed in the insulating member 20. Therefore, the voltage $V_1$ between the ground electrode 40 and the electrode 10 amplified by the first amplifier 80A is given by the same formula as the above-mentioned Formula (12).

Since Vb is considered to be constant in the above Formula (12), the state of contact between the insulating member 20 and the organ 70 can be evaluated by measuring the voltage $V_1$. Also, when Vb changes periodically, the contact state between the insulating member 20 and the organ 70 can be evaluated by measuring the voltage $V_1$ at the same cycle as that of Vb.

The present invention was described above through reference to a preferred embodiment, but this description should not be considered limiting in nature, and of course various modifications are possible. For instance, in the above embodiment, a balloon in the form of a hollow pouch was described as an example of the insulating member 20, but this is not the only option, as long as the electrode 10 is covered by the insulating member 20. Alternatively, the electrode 10 may be covered by the insulating member 20 via the conductive fluid 21.

In the above embodiment, the reference ground electrode 40 was disposed on the surface 60 of a living body, but the ground electrode 40 may be disposed inside the living body. As a result, since the living body itself has a shielding effect, the electric potential at the organ can be measured with less noise.

Also, in the above embodiment, the outer peripheral face of the insulating member 20 was brought into contact with the inner wall face (inner peripheral shape) of the organ 70 in a ring shape, and in this state the electric potential at the contact site was measured with the electrode 10 disposed in the insulating member 20, but this is not the only option, and the insulating member 20 may be pressed against a flat site and the electric potential at the contact site measured with the electrode 10 disposed in the insulating member 20. For example, the insulating member 20 may be pressed against the flat inner wall face of an organ, and the electric potential at the contact site may be measured with the electrode 10 while the insulating member 20 is deformed and put in contact so as to conform to the surface shape of the flat site.

In the above embodiment, an example of an in vivo potential measurement device was given in which the contact state between the insulating member 20 and the organ 70 was evaluated in ablation treatment, but this is not the only option, and the device can also be applied when the insulating member 20 is inserted into an organ of a living body, and the contact state between the insulating member 20 and the organ 70 is evaluated in measuring the electric potential at a specific site (e.g., contact site) on the inner wall face of the organ.

In understanding the scope of the present invention, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Also, the terms "part," "section," "portion," "member" or "element" when used in the singular can have the dual meaning of a single part or a plurality of parts unless otherwise stated.

While only selected embodiments have been chosen to illustrate the present invention, it will be apparent to those skilled in the art from this disclosure that various changes and modifications can be made herein without departing from the scope of the invention as defined in the appended claims. For example, unless specifically stated otherwise, the size, shape, location or orientation of the various components can be changed as needed and/or desired so long as the changes do not substantially affect their intended function. Unless specifically stated otherwise, components that are shown directly connected or contacting each other can have intermediate structures disposed between them so long as the changes do not substantially affect their intended function. The functions of one element can be performed by two, and vice versa unless specifically stated otherwise. The structures and functions of one embodiment can be adopted in another embodiment. It is not necessary for all advantages to be present in a particular embodiment at the same time. Every feature which is unique from the prior art, alone or in combination with other features, also should be considered a separate description of further inventions by the applicant, including the structural and/or functional concepts embodied by such feature(s). Thus, the foregoing descriptions of the embodiments according to the present invention are provided for illustration only, and not for the purpose of limiting the invention as defined by the appended claims and their equivalents.

What is claimed is:

1. An in vivo potential measurement device comprising:
   an insulating member having an electrode that is disposed inside thereof, the insulating member being configured to be inserted into an organ of a living body such that an outer peripheral face of the insulating member makes contact with an inner wall face of the organ at a contact site, the electrode being configured to sense electric potential at the contact site;
   an amplifier configured to amplify the electric potential sensed by the electrode to obtain output voltage, the amplifier being configured to be disposed outside the living body; and
   a processor to which the output voltage obtained by amplifying the electric potential with the amplifier is input,
   the amplifier having input capacitance Cin and input resistance Rin that satisfy $Cin/Ce > 0.1$ and $1/(2\pi f Ce Rin) > 0.1$, where Ce represents capacitance of the insulating member at the contact site, and f represents frequency of the electric potential at the contact site on the inner wall face of the organ, and
   the processor being configured to evaluate a contact state between the outer peripheral face of the insulating member and the inner wall face of the organ using the output voltage obtained by amplifying the electric potential with the amplifier.

2. The in vivo potential measurement device according to claim 1, wherein
   the outer peripheral face of the insulating member is formed by a member that is deformable or expandable to match a shape of the contact site.

3. The in vivo potential measurement device according to claim 2, wherein
   the electrode is configured to sense the electric potential at the contact site while the outer peripheral face of the insulating member makes contact with the inner wall face of the organ in a ring shape.

4. The in vivo potential measurement device according to claim 2, wherein
   the insulating member includes a hollow pouch, and
   the electrode is configured to sense the electric potential at the contact site while a conductive fluid is injected into the insulating member and the outer peripheral face of the insulating member makes contact with the inner wall face of the organ.

5. The in vivo potential measurement device according to claim 2, wherein
   the insulating member is configured to be sandwiched between the electrode and the inner wall face of the organ to form a capacitance coupled electrode.

6. The in vivo potential measurement device according to claim 1, wherein the electrode is configured to sense the electric potential at the contact site while the outer peripheral face of the insulating member makes contact with the inner wall face of the organ in a ring shape.

7. The in vivo potential measurement device according to claim 1, wherein
   the insulating member includes a hollow pouch, and
   the electrode is configured to sense the electric potential at the contact site while a conductive fluid is injected into the insulating member and the outer peripheral face of the insulating member makes contact with the inner wall face of the organ.

8. The in vivo potential measurement device according to claim 7, wherein
   the insulating member is configured to cauterize the contact site by passing a high-frequency current through the electrode to heat the conductive fluid while the outer peripheral face of the insulating member makes contact with the inner wall face of the organ.

9. The in vivo potential measurement device according to claim 1, wherein
   the insulating member is configured to be sandwiched between the electrode and the inner wall face of the organ to form a capacitance coupled electrode.

10. An in vivo potential measurement device comprising:
an insulating member having an electrode that is disposed inside thereof, the insulating member being configured to be inserted into an organ of a living body such that an outer peripheral face of the insulating member makes contact with an inner wall face of the organ at a contact site, the electrode being configured to sense electric potential at the contact site;
an amplifier configured to amplify the electric potential sensed by the electrode to obtain output voltage, the amplifier being configured to be disposed outside the living body; and
a processor to which the output voltage obtained by amplifying the electric potential with the amplifier is input,
the amplifier including
a first amplifier having input capacitance Cin and input resistance Rin that satisfy $Cin/Ce > 0.1$ and $1/(2\pi f CeRin) > 0.1$, and
a second amplifier having input capacitance Cin and input resistance Rin that satisfy $Cin/Ce < 0.01$ and $1/(2\pi f CeRin) < 0.01$, where Ce represents capacitance of the insulating member at the contact site, and f represents frequency of the electric potential at the contact site on the inner wall face of the organ, and
the processor being configured to evaluate a contact state between the outer peripheral face of the insulating member and the inner wall face of the organ using a voltage ratio $V_1/V_2$ of a first voltage $V_1$ obtained by amplifying the electric potential with the first amplifier and a second voltage $V_2$ obtained by amplifying the electric potential with the second amplifier.

11. The in vivo potential measurement device according to claim 10, further comprising
a switch configured to switch such that the electric potential sensed by the electrode is measured by either the first amplifier or the second amplifier,
the first voltage $V_1$ and the second voltage $V_2$ being continuously measured using the first amplifier and the second amplifier by switching at the same cycle timing with the switch.

12. The in vivo potential measurement device according to claim 11, wherein
the outer peripheral face of the insulating member is formed by a member that is deformable and expandable to match a shape of the contact site.

13. The in vivo potential measurement device according to claim 11, wherein
the electrode is configured to sense the electric potential at the contact site while the outer peripheral face of the insulating member makes contact with the inner wall face of the organ in a ring shape.

14. The in vivo potential measurement device according to claim 11, wherein
the insulating member includes a hollow pouch, and
the electrode is configured to sense the electric potential at the contact site while a conductive fluid is injected into the insulating member and the outer peripheral face of the insulating member makes contact with the inner wall face of the organ.

15. The in vivo potential measurement device according to claim 11, wherein
the insulating member is configured to be sandwiched between the electrode and the inner wall face of the organ to form a capacitance coupled electrode.

16. The in vivo potential measurement device according to claim 10, wherein
the processor is configured to evaluate the contact state between the outer peripheral face of the insulating member and the inner wall face of the organ immediately after cauterization by measuring the first voltage Vi and the second voltage $V_2$ after passing a high-frequency current through the electrode to cauterize the contact site while the outer peripheral face of the insulating member makes contact with the inner wall face of the organ.

17. The in vivo potential measurement device according to claim 10, wherein
the outer peripheral face of the insulating member is formed by a member that is deformable and expandable to match a shape of the contact site.

18. The in vivo potential measurement device according to claim 10, wherein
the electrode is configured to sense the electric potential at the contact site while the outer peripheral face of the insulating member makes contact with the inner wall face of the organ in a ring shape.

19. The in vivo potential measurement device according to claim 10, wherein
the insulating member includes a hollow pouch, and
the electrode is configured to sense the electric potential at the contact site while a conductive fluid is injected into the insulating member and the outer peripheral face of the insulating member makes contact with the inner wall face of the organ.

20. The in vivo potential measurement device according to claim 10, wherein
the insulating member is configured to be sandwiched between the electrode and the inner wall face of the organ to form a capacitance coupled electrode.

* * * * *